(12) United States Patent
Leisinger (10) Patent No.: US 9,717,545 B2
(45) Date of Patent: Aug. 1, 2017

(54) TAPER DISENGAGEMENT TOOL

(71) Applicant: DEPUY SYNTHES PRODUCTS, LLC, Raynham, MA (US)

(72) Inventor: Steven R Leisinger, Silver Lake, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 76 days.

(21) Appl. No.: 14/025,919

(22) Filed: Sep. 13, 2013

(65) Prior Publication Data

US 2014/0012272 A1  Jan. 9, 2014

Related U.S. Application Data

(62) Division of application No. 11/927,811, filed on Oct. 30, 2007, now Pat. No. 8,556,912.

(51) Int. Cl.
| | | |
|---|---|---|
| *A61B 17/58* | (2006.01) | |
| *A61B 17/92* | (2006.01) | |
| *A61F 2/46* | (2006.01) | |
| *B25B 27/02* | (2006.01) | |
| *A61F 2/30* | (2006.01) | |

(52) U.S. Cl.
CPC ............ *A61B 17/92* (2013.01); *A61F 2/4637* (2013.01); *B25B 27/023* (2013.01); *A61F 2002/30332* (2013.01); *A61F 2002/4641* (2013.01); *A61F 2220/0033* (2013.01)

(58) Field of Classification Search
CPC .................................................. A61F 2/4637
USPC .................................................. 606/99–100
See application file for complete search history.

(56) References Cited

U.S. PATENT DOCUMENTS

| | | | |
|---|---|---|---|
| 422,013 | A | 2/1890 | Ekstrom |
| 650,795 | A | 5/1900 | Maxwell |
| 742,521 | A | 10/1903 | Terry |
| 784,243 | A | 3/1905 | Whalley |
| 1,029,402 | A | 6/1912 | Ritter |
| 1,241,846 | A | 10/1917 | Grons |
| 1,383,304 | A | 7/1921 | Hughes |
| 1,423,649 | A | 7/1922 | Daniel |
| 1,534,692 | A | 4/1925 | Davis |
| 1,661,682 | A | 3/1928 | Scherner |

(Continued)

FOREIGN PATENT DOCUMENTS

| | | |
|---|---|---|
| DE | 2823406 A1 | 12/1978 |
| DE | 3023942 A1 | 1/1982 |

(Continued)

OTHER PUBLICATIONS

Zimmer, "Metasul LDH Large Diameter Head," Surgical Technique Enhancing Stability and Increasing Range of Motion, available at least as early as Sep. 28, 2006 (19 pages).

(Continued)

*Primary Examiner* — Matthew Lawson (57) ABSTRACT

A kit including a first component having a male taper and a second component having an internal bore with a female taper. The first component and second component being engageable via the male and female tapers. The kit further including a disassembly tool having a body and an expandable portion separable from the body, such that the expandable portion has an initial outer diameter equal to the inner diameter of the internal bore of the second component.

9 Claims, 5 Drawing Sheets

(56) References Cited

U.S. PATENT DOCUMENTS

| | | |
|---|---|---|
| 2,234,824 A | 3/1941 | Kingston |
| 2,248,054 A | 7/1941 | Becker |
| 2,487,331 A | 11/1949 | Greene |
| 2,626,023 A * | 1/1953 | Lear .................... 411/60.1 |
| 2,661,033 A | 12/1953 | Daniel |
| 2,711,196 A | 6/1955 | Daniel |
| 2,834,099 A | 5/1958 | Gasper |
| 2,834,382 A | 5/1958 | Daniel |
| 2,856,637 A | 10/1958 | Daniel |
| 2,864,282 A | 12/1958 | Daniel |
| 2,877,936 A | 3/1959 | Daniel |
| 2,895,154 A | 7/1959 | Daniel |
| 2,902,596 A | 9/1959 | Daniel |
| 2,914,224 A | 11/1959 | Daniel |
| 2,944,373 A | 7/1960 | Mentley |
| 2,955,905 A | 10/1960 | Daniel |
| 2,957,610 A | 10/1960 | Daniel |
| 2,974,699 A | 3/1961 | Boles |
| 2,975,944 A | 3/1961 | Daniel |
| 2,977,726 A | 4/1961 | Daniel |
| 2,981,035 A | 4/1961 | Mentley |
| 2,994,461 A | 8/1961 | Daniel |
| 2,994,988 A | 8/1961 | Mentley |
| 3,048,307 A | 8/1962 | Daniel |
| 3,059,278 A | 10/1962 | Daniel |
| 3,071,862 A | 1/1963 | Daniel |
| 3,077,877 A | 2/1963 | Daniel |
| 3,092,934 A | 6/1963 | Daniel |
| 3,092,935 A | 6/1963 | Daniel |
| 3,101,875 A | 8/1963 | Daniel |
| 3,135,136 A | 6/1964 | Mentley |
| 3,177,507 A | 4/1965 | Becker |
| 3,180,532 A | 4/1965 | Daniel |
| 3,200,484 A | 8/1965 | Garman |
| 3,220,311 A | 11/1965 | Anthony |
| 3,250,745 A | 5/1966 | Daniel |
| 3,293,987 A | 12/1966 | Daniel |
| 3,300,833 A | 1/1967 | Daniel |
| 3,301,134 A | 1/1967 | Daniel |
| 3,319,526 A | 5/1967 | Daniel |
| 3,331,115 A | 7/1967 | Daniel |
| 3,335,639 A | 8/1967 | Daniel |
| 3,424,783 A | 1/1969 | Harper |
| 3,443,478 A | 5/1969 | Daniel |
| 3,451,111 A | 6/1969 | Daniel |
| 3,479,387 A | 11/1969 | Daniels |
| 3,479,388 A | 11/1969 | Daniels |
| 3,483,175 A | 12/1969 | Harper |
| 3,494,752 A | 2/1970 | Daniel |
| 3,499,920 A | 3/1970 | Daniels |
| 3,541,868 A | 11/1970 | Hall |
| 3,580,027 A | 5/1971 | Daniel |
| 3,580,029 A | 5/1971 | Daniel |
| 3,604,235 A | 9/1971 | Motz |
| 3,629,981 A | 12/1971 | McCaffery |
| 3,631,703 A | 1/1972 | Bregi |
| 3,633,583 A | 1/1972 | Fishbein |
| 3,668,139 A | 6/1972 | Daniels |
| 3,673,887 A | 7/1972 | Daniel |
| 3,679,728 A | 7/1972 | Morgan |
| 3,679,729 A | 7/1972 | Daniels |
| 3,691,718 A | 9/1972 | Woodruff |
| 3,700,957 A | 10/1972 | Daniels |
| 3,705,513 A | 12/1972 | Daniel |
| 3,749,365 A | 7/1973 | Van Gompel |
| 3,754,586 A | 8/1973 | Daniels |
| 3,810,312 A | 5/1974 | Carson |
| 3,849,322 A | 11/1974 | Wendler |
| 3,862,483 A | 1/1975 | Kloster |
| 3,869,394 A | 3/1975 | Daniels |
| 3,889,558 A | 6/1975 | Duncan |
| 3,912,727 A | 10/1975 | Daniels |
| 3,987,499 A | 10/1976 | Scharbach |
| 4,004,581 A | 1/1977 | Heimke |
| 4,009,712 A | 3/1977 | Burstein |
| 4,035,988 A | 7/1977 | Daniels |
| 4,051,559 A | 10/1977 | Pifferi |
| D246,507 S | 11/1977 | Danielson |
| 4,115,875 A | 9/1978 | Rambert |
| 4,116,200 A | 9/1978 | Braun |
| 4,150,909 A | 4/1979 | Hibarger |
| D257,533 S | 11/1980 | Bevilacqua |
| D258,957 S | 4/1981 | Bevilacqua |
| 4,305,394 A | 12/1981 | Bertuch, Jr. |
| D266,768 S | 11/1982 | Bevilacqua |
| D267,151 S | 12/1982 | Bruce |
| 4,398,074 A | 8/1983 | Danielson |
| 4,420,864 A | 12/1983 | Hoyt |
| 4,457,306 A | 7/1984 | Borzone |
| 4,458,420 A | 7/1984 | Davis |
| D275,006 S | 8/1984 | Danielson |
| 4,473,070 A | 9/1984 | Matthews |
| 4,538,886 A | 9/1985 | Townsend |
| D282,246 S | 1/1986 | Thomas |
| D282,350 S | 1/1986 | Thomas |
| 4,601,289 A | 7/1986 | Chiarizzio |
| D285,073 S | 8/1986 | Danielson |
| D285,198 S | 8/1986 | Danielson |
| 4,608,055 A | 8/1986 | Morrey |
| D286,198 S | 10/1986 | Bancroft |
| D286,285 S | 10/1986 | Danielson |
| D287,494 S | 12/1986 | Danielson |
| D289,155 S | 4/1987 | Brooks |
| 4,658,808 A | 4/1987 | Link |
| D290,399 S | 6/1987 | Kitchens |
| 4,670,015 A | 6/1987 | Freeman |
| 4,686,971 A | 8/1987 | Harris |
| 4,686,978 A | 8/1987 | Wadsworth |
| 4,693,724 A | 9/1987 | Rhenter |
| 4,710,946 A | 12/1987 | Hinch |
| 4,716,894 A | 1/1988 | Lazzeri |
| 4,738,256 A | 4/1988 | Freeman |
| 4,777,942 A | 10/1988 | Frey |
| 4,830,147 A | 5/1989 | Kawada |
| D303,114 S | 8/1989 | Danielson |
| D304,587 S | 11/1989 | Danielson |
| 4,891,545 A | 1/1990 | Capek |
| 4,917,530 A | 4/1990 | Engelhardt |
| 4,923,422 A | 5/1990 | Capek |
| 4,938,773 A | 7/1990 | Strand |
| 4,959,066 A | 9/1990 | Dunn |
| 4,969,911 A | 11/1990 | Greene |
| D313,233 S | 12/1990 | Andrews, Sr. |
| D315,343 S | 3/1991 | Andrews |
| 4,997,621 A | 3/1991 | Johansson |
| 5,002,578 A | 3/1991 | Luman |
| 5,002,581 A | 3/1991 | Paxson |
| 5,015,255 A | 5/1991 | Kuslich |
| 5,016,858 A | 5/1991 | Mitchell |
| 5,020,519 A | 6/1991 | Hayes |
| D318,051 S | 7/1991 | Danielson |
| 5,033,180 A | 7/1991 | Colson |
| D319,439 S | 8/1991 | Danielson |
| 5,047,033 A | 9/1991 | Fallin |
| 5,049,150 A | 9/1991 | Cozad |
| D320,985 S | 10/1991 | Danielson |
| 5,053,037 A | 10/1991 | Lackey |
| 5,057,112 A | 10/1991 | Sherman |
| 5,060,505 A | 10/1991 | Tury |
| 5,061,271 A | 10/1991 | Van Zile |
| 5,080,685 A | 1/1992 | Bolesky |
| D323,657 S | 2/1992 | Danielson |
| 5,099,714 A | 3/1992 | Hutchison |
| 5,100,407 A | 3/1992 | Conrad |
| 5,108,452 A | 4/1992 | DeMane |
| 5,133,588 A | 7/1992 | Hutchinson |
| 5,135,529 A | 8/1992 | Paxson |
| 5,162,626 A | 11/1992 | Hutchison |
| 5,171,055 A | 12/1992 | Hutchison |
| 5,171,244 A | 12/1992 | Caspari |
| 5,181,928 A | 1/1993 | Bolesky |
| 5,184,017 A | 2/1993 | Tury |
| 5,190,548 A | 3/1993 | Davis |
| 5,190,550 A | 3/1993 | Miller |

(56) References Cited

U.S. PATENT DOCUMENTS

| | | |
|---|---|---|
| 5,192,283 A | 3/1993 | Ling |
| 5,197,989 A | 3/1993 | Hinckfuss |
| 5,201,882 A | 4/1993 | Paxson |
| 5,207,680 A | 5/1993 | Dietz |
| 5,218,814 A | 6/1993 | Teal |
| D337,639 S | 7/1993 | Beckman |
| 5,228,459 A | 7/1993 | Caspari |
| D338,473 S | 8/1993 | Patterson |
| 5,238,267 A | 8/1993 | Hutchison |
| 5,247,171 A | 9/1993 | Wlodarczyk |
| D340,461 S | 10/1993 | Patterson |
| 5,263,498 A | 11/1993 | Caspari |
| 5,290,313 A | 3/1994 | Heldreth |
| 5,304,181 A | 4/1994 | Caspari |
| D346,979 S | 5/1994 | Stalcup |
| 5,331,124 A | 7/1994 | Danielson |
| 5,336,226 A | 8/1994 | McDaniel |
| 5,342,363 A | 8/1994 | Richelsoph |
| 5,342,366 A | 8/1994 | Whiteside |
| 5,344,423 A | 9/1994 | Dietz |
| 5,345,483 A | 9/1994 | Johansson |
| 5,352,231 A | 10/1994 | Brumfield |
| D352,521 S | 11/1994 | Sculler |
| D353,394 S | 12/1994 | Stefanski |
| 5,370,706 A | 12/1994 | Bolesky |
| 5,372,209 A | 12/1994 | Raihert |
| D355,186 S | 2/1995 | Danielson |
| D355,187 S | 2/1995 | Danielson |
| 5,387,218 A | 2/1995 | Meswania |
| 5,395,376 A | 3/1995 | Caspari |
| D357,315 S | 4/1995 | Dietz |
| 5,403,320 A | 4/1995 | Luman |
| 5,405,404 A | 4/1995 | Gardner |
| 5,409,492 A | 4/1995 | Jones |
| 5,415,659 A | 5/1995 | Lee |
| 5,420,910 A | 5/1995 | Rudokas |
| D359,064 S | 6/1995 | Sculler |
| 5,422,478 A | 6/1995 | Wlodarczyk |
| 5,457,100 A | 10/1995 | Daniel |
| 5,459,294 A | 10/1995 | Danielson |
| D364,621 S | 11/1995 | Clarke |
| 5,468,243 A | 11/1995 | Halpern |
| 5,470,336 A | 11/1995 | Ling |
| 5,474,559 A | 12/1995 | Bertin |
| 5,476,466 A | 12/1995 | Barrette |
| D365,824 S | 1/1996 | Danielson |
| 5,486,180 A | 1/1996 | Dietz |
| 5,496,324 A | 3/1996 | Barnes |
| 5,507,815 A | 4/1996 | Wagner |
| 5,507,824 A | 4/1996 | Lennox |
| 5,507,830 A | 4/1996 | DeMane |
| 5,507,833 A | 4/1996 | Bohn |
| 5,519,929 A | 5/1996 | Bleckman |
| 5,527,316 A | 6/1996 | Stone |
| 5,528,640 A | 6/1996 | Johansson |
| 5,534,005 A | 7/1996 | Tokish, Jr. |
| 5,540,687 A | 7/1996 | Fairley |
| 5,540,694 A | 7/1996 | DeCarlo, Jr. |
| 5,555,551 A | 9/1996 | Rudokas |
| 5,569,255 A | 10/1996 | Burke |
| D376,527 S | 12/1996 | Apolinski |
| 5,591,233 A | 1/1997 | Kelman |
| 5,593,411 A | 1/1997 | Stalcup |
| 5,593,452 A | 1/1997 | Higham |
| 5,600,892 A | 2/1997 | Peugh |
| 5,601,563 A | 2/1997 | Burke |
| 5,601,567 A | 2/1997 | Swajger |
| 5,607,269 A | 3/1997 | Dowd |
| 5,607,431 A | 3/1997 | Dudasik |
| D379,578 S | 6/1997 | Daniels |
| 5,643,271 A | 7/1997 | Sederholm |
| 5,645,607 A | 7/1997 | Hickey |
| 5,653,714 A | 8/1997 | Dietz |
| 5,653,764 A | 8/1997 | Murphy |
| 5,653,765 A | 8/1997 | McTighe |
| 5,658,349 A | 8/1997 | Brooks |
| 5,663,993 A | 9/1997 | Danielson |
| 5,669,812 A | 9/1997 | Schockemoehl |
| 5,683,395 A | 11/1997 | Mikhail |
| D387,962 S | 12/1997 | Apolinski |
| D387,963 S | 12/1997 | Clark |
| 5,697,932 A | 12/1997 | Smith |
| 5,702,480 A | 12/1997 | Kropf |
| 5,702,487 A | 12/1997 | Averill |
| 5,715,672 A | 2/1998 | Schockemoehl |
| D392,534 S | 3/1998 | Degen |
| D392,866 S | 3/1998 | Degen |
| 5,725,592 A | 3/1998 | White |
| 5,728,128 A | 3/1998 | Crickenberger |
| 5,735,857 A | 4/1998 | Lane |
| 5,743,915 A | 4/1998 | Bertin |
| 5,752,972 A | 5/1998 | Hoogeboom |
| 5,755,803 A | 5/1998 | Haines |
| 5,766,261 A | 6/1998 | Neal |
| 5,769,855 A | 6/1998 | Bertin |
| 5,776,200 A | 7/1998 | Johnson |
| 5,782,921 A | 7/1998 | Colleran |
| 5,792,143 A | 8/1998 | Samuelson |
| 5,800,553 A | 9/1998 | Albrektsson |
| 5,804,886 A | 9/1998 | Danielson |
| 5,810,827 A | 9/1998 | Haines |
| 5,810,829 A | 9/1998 | Elliott |
| 5,810,830 A | 9/1998 | Noble |
| 5,824,097 A | 10/1998 | Gabriel |
| 5,849,015 A | 12/1998 | Haywood |
| 5,850,162 A | 12/1998 | Danielsons |
| 5,853,415 A | 12/1998 | Bertin |
| 5,858,020 A | 1/1999 | Johnson |
| 5,858,828 A | 1/1999 | Seliskar |
| 5,860,969 A | 1/1999 | White |
| 5,860,981 A | 1/1999 | Bertin |
| 5,876,459 A | 3/1999 | Powell |
| 5,879,354 A | 3/1999 | Haines |
| 5,879,391 A | 3/1999 | Slamin |
| 5,890,966 A | 4/1999 | Costain |
| 5,902,340 A | 5/1999 | White |
| 5,906,644 A | 5/1999 | Powell |
| 5,908,423 A | 6/1999 | Kashuba |
| 5,919,195 A | 7/1999 | Wilson |
| 5,923,422 A | 7/1999 | Keens |
| 5,935,172 A | 8/1999 | Ochoa |
| 5,938,701 A | 8/1999 | Hiernard |
| 5,950,121 A | 9/1999 | Kaminsky |
| 5,951,606 A | 9/1999 | Burke |
| 5,954,460 A | 9/1999 | Degen |
| 5,957,768 A | 9/1999 | Schockemoehl |
| 5,957,925 A | 9/1999 | Cook |
| 5,966,599 A | 10/1999 | Walker |
| 5,968,049 A | 10/1999 | Da Rold |
| 5,973,064 A | 10/1999 | Zhao |
| 5,976,145 A | 11/1999 | Kennefick, III |
| 5,976,147 A | 11/1999 | LaSalle |
| 5,976,188 A | 11/1999 | Dextradeur |
| 5,993,455 A | 11/1999 | Noble |
| 5,996,812 A | 12/1999 | Sokol, Jr. |
| 5,997,419 A | 12/1999 | Daniels |
| 6,013,082 A | 1/2000 | Hiernard |
| 6,045,556 A | 4/2000 | Cohen |
| 6,048,365 A | 4/2000 | Burrows |
| 6,054,895 A | 4/2000 | Danielsons |
| 6,056,084 A | 5/2000 | Schockemoehl |
| 6,056,754 A | 5/2000 | Haines |
| 6,058,301 A | 5/2000 | Daniels |
| 6,059,528 A | 5/2000 | Danielson |
| 6,063,123 A | 5/2000 | Burrows |
| 6,069,048 A | 5/2000 | Daniel |
| 6,071,311 A | 6/2000 | O'Neil |
| 6,077,783 A | 6/2000 | Allman |
| 6,080,162 A | 6/2000 | Dye |
| 6,090,146 A | 7/2000 | Rozow, III |
| 6,096,625 A | 8/2000 | Daniel |
| 6,110,179 A | 8/2000 | Flivik |
| 6,117,138 A | 9/2000 | Burrows |
| 6,120,507 A | 9/2000 | Allard |

(56) References Cited

U.S. PATENT DOCUMENTS

| | | |
|---|---|---|
| 6,121,147 A | 9/2000 | Daniel |
| 6,126,694 A | 10/2000 | Gray, Jr. |
| 6,136,035 A | 10/2000 | Lob |
| 6,139,581 A | 10/2000 | Engh |
| 6,149,687 A | 11/2000 | Gray, Jr. |
| 6,159,214 A | 12/2000 | Michelson |
| 6,162,226 A | 12/2000 | DeCarlo, Jr. |
| 6,165,177 A | 12/2000 | Wilson |
| 6,179,116 B1 | 1/2001 | Noniewicz |
| 6,179,877 B1 | 1/2001 | Burke |
| 6,181,925 B1 | 1/2001 | Kaminsky |
| 6,185,416 B1 | 2/2001 | Rudokas |
| 6,187,012 B1 | 2/2001 | Masini |
| 6,193,725 B1 * | 2/2001 | Macey .................. A61B 17/921 606/104 |
| 6,193,759 B1 | 2/2001 | Ro |
| 6,197,064 B1 | 3/2001 | Haines |
| 6,197,065 B1 | 3/2001 | Martin |
| 6,201,253 B1 | 3/2001 | Allman |
| 6,206,884 B1 | 3/2001 | Masini |
| 6,219,538 B1 | 4/2001 | Kaminsky |
| 6,224,605 B1 | 5/2001 | Anderson |
| 6,232,721 B1 | 5/2001 | Danielsons |
| 6,235,590 B1 | 5/2001 | Daniel |
| 6,238,435 B1 * | 5/2001 | Meulink et al. ........... 623/22.12 |
| 6,238,436 B1 | 5/2001 | Lob |
| D443,882 S | 6/2001 | Daniels |
| 6,241,847 B1 | 6/2001 | Allman |
| 6,242,978 B1 | 6/2001 | Danielsons |
| 6,258,093 B1 | 7/2001 | Edwards |
| 6,258,095 B1 | 7/2001 | Lombardo |
| 6,258,097 B1 | 7/2001 | Cook |
| 6,260,279 B1 | 7/2001 | Apolinski |
| 6,263,998 B1 | 7/2001 | Schockemoehl |
| 6,264,699 B1 | 7/2001 | Noiles |
| 6,270,502 B1 | 8/2001 | Stulberg |
| 6,281,935 B1 | 8/2001 | Twitchell |
| 6,285,871 B1 | 9/2001 | Daniels |
| 6,287,342 B1 | 9/2001 | Copf |
| 6,310,410 B1 | 10/2001 | Lin |
| D450,304 S | 11/2001 | Daniels |
| 6,316,817 B1 | 11/2001 | Seliskar |
| 6,318,651 B1 | 11/2001 | Spiering |
| 6,319,286 B1 | 11/2001 | Fernandez |
| 6,330,845 B1 | 12/2001 | Meulink |
| 6,332,886 B1 | 12/2001 | Green |
| 6,335,766 B1 | 1/2002 | Twitchell |
| 6,354,908 B2 | 3/2002 | Allman |
| 6,355,068 B1 | 3/2002 | Doubler |
| 6,355,532 B1 | 3/2002 | Seliskar |
| 6,361,563 B2 | 3/2002 | Terrill Grisoni |
| 6,366,422 B1 | 4/2002 | Daniel |
| 6,372,520 B1 | 4/2002 | Hsia |
| D457,176 S | 5/2002 | Daniels |
| 6,382,276 B1 | 5/2002 | Daniels |
| D458,947 S | 6/2002 | Svetlik |
| 6,400,415 B1 | 6/2002 | Danielsons |
| 6,406,217 B1 | 6/2002 | Daniel |
| 6,419,147 B1 | 7/2002 | Daniel |
| 6,422,562 B1 | 7/2002 | Daniel |
| 6,422,816 B1 | 7/2002 | Danielson |
| 6,428,578 B2 | 8/2002 | White |
| 6,432,110 B1 | 8/2002 | Richelsoph |
| 6,432,141 B1 | 8/2002 | Stocks |
| 6,440,139 B2 | 8/2002 | Michelson |
| D467,485 S | 12/2002 | Daniels |
| 6,488,713 B1 | 12/2002 | Hershberger |
| 6,491,696 B1 | 12/2002 | Kunkel |
| D468,180 S | 1/2003 | Bruno |
| 6,505,684 B2 | 1/2003 | Rayssiguier |
| 6,508,841 B2 | 1/2003 | Martin |
| D469,671 S | 2/2003 | Prell |
| 6,517,581 B2 | 2/2003 | Blamey |
| RE38,058 E | 4/2003 | Fallin |
| 6,565,029 B2 | 5/2003 | Zweighaft |
| 6,568,618 B1 | 5/2003 | Vanderheyden |
| 6,589,284 B1 | 7/2003 | Silberer |
| 6,589,285 B2 | 7/2003 | Penenberg |
| 6,600,516 B1 | 7/2003 | Danielsons |
| 6,609,900 B2 | 8/2003 | Lucke |
| 6,613,091 B1 | 9/2003 | Zdeblick |
| 6,663,616 B1 | 12/2003 | Roth |
| 6,676,706 B1 | 1/2004 | Mears |
| 6,679,917 B2 | 1/2004 | Ek |
| 6,682,568 B2 | 1/2004 | Despres, III |
| 6,692,530 B2 * | 2/2004 | Doubler .................... A61F 2/36 606/62 |
| 6,700,359 B2 | 3/2004 | Daniels |
| 6,702,854 B1 | 3/2004 | Cheal |
| 6,706,072 B2 | 3/2004 | Dwyer |
| 6,706,621 B2 | 3/2004 | Cox |
| 6,712,825 B2 | 3/2004 | Aebi |
| 6,723,129 B2 | 4/2004 | Dwyer |
| 6,740,090 B1 | 5/2004 | Cragg |
| 6,743,235 B2 | 6/2004 | Subba Rao |
| 6,744,243 B2 | 6/2004 | Daniels |
| 6,751,266 B1 | 6/2004 | Danielsons |
| 6,755,841 B2 | 6/2004 | Fraser |
| 6,770,100 B2 | 8/2004 | Draenert |
| 6,793,208 B1 | 9/2004 | Riddle, Jr. |
| D497,499 S | 10/2004 | Daniel |
| 6,811,376 B2 | 11/2004 | Arel |
| 6,812,792 B2 | 11/2004 | Mattsson |
| 6,824,552 B2 | 11/2004 | Robison |
| 6,840,944 B2 | 1/2005 | Suddaby |
| 6,846,314 B2 | 1/2005 | Shapira |
| 6,856,029 B1 | 2/2005 | Daniel |
| 6,870,160 B1 | 3/2005 | Daniel |
| 6,875,218 B2 | 4/2005 | Dye |
| 6,883,217 B2 * | 4/2005 | Barrette et al. .................. 29/256 |
| D505,611 S | 5/2005 | Daniel |
| 6,905,515 B1 | 6/2005 | Gilbertson |
| 6,911,048 B2 | 6/2005 | Fernandez |
| 6,949,101 B2 | 9/2005 | McCleary |
| 6,990,691 B2 | 1/2006 | Klotz |
| 6,997,930 B1 | 2/2006 | Jäggi |
| 7,001,392 B2 | 2/2006 | McGovern |
| 7,008,420 B2 | 3/2006 | Okada |
| 7,022,141 B2 | 4/2006 | Dwyer |
| 7,066,042 B2 | 6/2006 | Andrews |
| 7,074,224 B2 | 7/2006 | Daniels |
| 7,188,556 B1 | 3/2007 | Rinner |
| 7,189,242 B2 | 3/2007 | Boyd |
| 7,204,851 B2 | 4/2007 | Trieu |
| 7,297,166 B2 | 11/2007 | Dwyer |
| 7,363,838 B2 | 4/2008 | Abdelgany |
| 7,373,709 B2 | 5/2008 | Fernando |
| 7,387,635 B2 | 6/2008 | Keller |
| 7,425,214 B1 | 9/2008 | McCarthy |
| 7,431,723 B2 | 10/2008 | Hazebrouck |
| 7,468,078 B2 * | 12/2008 | Sederholm .......... A61F 2/30734 623/22.42 |
| 7,582,092 B2 | 9/2009 | Jones |
| 7,585,329 B2 | 9/2009 | McCleary |
| 7,601,155 B2 | 10/2009 | Petersen |
| 7,641,658 B2 | 1/2010 | Shaolian |
| 8,696,758 B2 | 4/2014 | Hood |
| 8,702,807 B2 | 4/2014 | Hood |
| 8,900,246 B2 | 12/2014 | Lashure |
| 8,998,919 B2 | 4/2015 | Jones |
| 2001/0001121 A1 | 5/2001 | Lombardo |
| 2001/0007957 A1 | 7/2001 | Martin |
| 2001/0016779 A1 | 8/2001 | Lubinus |
| 2001/0021621 A1 | 9/2001 | Moore |
| 2001/0021622 A1 | 9/2001 | Allman |
| 2001/0034526 A1 | 10/2001 | Kuslich |
| 2002/0004684 A1 | 1/2002 | Thomas |
| 2002/0038148 A1 | 3/2002 | Fernandez |
| 2002/0043296 A1 | 4/2002 | Daniels |
| 2002/0058999 A1 | 5/2002 | Dwyer |
| 2002/0059000 A1 | 5/2002 | Dwyer |
| 2002/0127115 A1 | 9/2002 | Lucke |
| 2002/0133233 A1 | 9/2002 | Blamey |
| 2002/0183758 A1 | 12/2002 | Middleton |

(56) References Cited

U.S. PATENT DOCUMENTS

| | | | |
|---|---|---|---|
| 2002/0195512 A1 | 12/2002 | Zweighft |
| 2003/0001551 A1 | 1/2003 | Daniels |
| 2003/0048003 A1 | 3/2003 | Daniels |
| 2003/0050645 A1 | 3/2003 | Parker |
| 2003/0071329 A1 | 4/2003 | Cox |
| 2003/0074080 A1 | 4/2003 | Murray |
| 2003/0093080 A1 | 5/2003 | Brown |
| 2003/0095368 A1 | 5/2003 | Daniels |
| 2003/0109882 A1 | 6/2003 | Shirado |
| 2003/0114933 A1 | 6/2003 | Bouttens |
| 2003/0130740 A1 | 7/2003 | Stocks |
| 2003/0149487 A1 | 8/2003 | Doubler |
| 2003/0171756 A1 | 9/2003 | Fallin |
| 2003/0171816 A1 | 9/2003 | Scifert |
| 2003/0180146 A1 | 9/2003 | Arel |
| 2003/0187449 A1 | 10/2003 | McCleary |
| 2003/0204269 A1 | 10/2003 | Gerbec |
| 2003/0220698 A1 | 11/2003 | Mears |
| 2003/0225417 A1 | 12/2003 | Fischell |
| 2003/0228033 A1 | 12/2003 | Daniel |
| 2004/0010262 A1 | 1/2004 | Parkinson |
| 2004/0010319 A1 | 1/2004 | McTighe |
| 2004/0015239 A1 | 1/2004 | Beguec |
| 2004/0017085 A1 | 1/2004 | Daniels |
| 2004/0054373 A1 | 3/2004 | Serra |
| 2004/0054419 A1 | 3/2004 | Serra |
| 2004/0058997 A1 | 3/2004 | Daniel |
| 2004/0064186 A1 | 4/2004 | McCleary |
| 2004/0066217 A1 | 4/2004 | Daniels |
| 2004/0073315 A1* | 4/2004 | Justin et al. ............... 623/20.15 |
| 2004/0092951 A1 | 5/2004 | Serra |
| 2004/0111861 A1 | 6/2004 | Barrette |
| 2004/0122437 A1* | 6/2004 | Dwyer et al. .................. 606/87 |
| 2004/0122439 A1 | 6/2004 | Dwyer |
| 2004/0122440 A1 | 6/2004 | Daniels |
| 2004/0122525 A1 | 6/2004 | Daniels |
| 2004/0130394 A1 | 7/2004 | Mattsson |
| 2004/0135233 A1 | 7/2004 | Cox |
| 2004/0147933 A1 | 7/2004 | McGovern |
| 2004/0167527 A1 | 8/2004 | Simon |
| 2004/0172138 A1 | 9/2004 | May |
| 2004/0172139 A1 | 9/2004 | Dwyer |
| 2004/0210471 A1 | 10/2004 | Luby |
| 2004/0211046 A1 | 10/2004 | Tally |
| 2004/0236342 A1 | 11/2004 | Ferree |
| 2004/0260297 A1 | 12/2004 | Padget |
| 2004/0267266 A1 | 12/2004 | Daniels |
| 2004/0267267 A1 | 12/2004 | Daniels |
| 2004/0267372 A1 | 12/2004 | Vanasse |
| 2004/0267373 A1 | 12/2004 | Dwyer |
| 2005/0004679 A1* | 1/2005 | Sederholm et al. ....... 623/22.42 |
| 2005/0010992 A1 | 1/2005 | Klotz |
| 2005/0015049 A1 | 1/2005 | Rioux |
| 2005/0033444 A1 | 2/2005 | Jones |
| 2005/0047239 A1 | 3/2005 | Takahashi |
| 2005/0078289 A1 | 4/2005 | Daniel |
| 2005/0081910 A1 | 4/2005 | Danielson |
| 2005/0085820 A1 | 4/2005 | Collins |
| 2005/0115391 A1 | 6/2005 | Baker |
| 2005/0154331 A1 | 7/2005 | Christie |
| 2005/0188878 A1 | 9/2005 | Baker |
| 2005/0209597 A1 | 9/2005 | Long |
| 2005/0222572 A1 | 10/2005 | Chana |
| 2005/0234461 A1 | 10/2005 | Burdulis |
| 2005/0234462 A1 | 10/2005 | Hershberger |
| 2005/0234559 A1 | 10/2005 | Fernandez |
| 2005/0240193 A1 | 10/2005 | Layne |
| 2005/0261702 A1 | 11/2005 | Oribe |
| 2005/0267937 A1 | 12/2005 | Daniels |
| 2005/0288676 A1 | 12/2005 | Schnieders |
| 2006/0015110 A1 | 1/2006 | Pepper |
| 2006/0015112 A1 | 1/2006 | McGovern |
| 2006/0024656 A1 | 2/2006 | Morris |
| 2006/0027027 A1 | 2/2006 | Serra |
| 2006/0058810 A1 | 3/2006 | Wozencroft |
| 2006/0106393 A1 | 5/2006 | Huebner |
| 2006/0217737 A1 | 9/2006 | Iversen |
| 2006/0260440 A1 | 11/2006 | Abdelgany |
| 2007/0005144 A1 | 1/2007 | Leisinger |
| 2007/0100464 A1 | 5/2007 | Meulink |
| 2007/0123908 A1 | 5/2007 | Jones |
| 2007/0179502 A1 | 8/2007 | Raynor |
| 2007/0233132 A1 | 10/2007 | Valla |
| 2007/0260315 A1 | 11/2007 | Foley |
| 2007/0299534 A1 | 12/2007 | Lewis |
| 2008/0065081 A1 | 3/2008 | Lechot |
| 2008/0071279 A1* | 3/2008 | Bandeira et al. ............... 606/90 |
| 2008/0077156 A1 | 3/2008 | Emstad |
| 2008/0091212 A1 | 4/2008 | Dwyer |
| 2008/0114367 A1 | 5/2008 | Meyer |
| 2008/0133024 A1 | 6/2008 | Meswania |
| 2008/0161811 A1 | 7/2008 | Daniels |
| 2008/0188878 A1 | 8/2008 | Young |
| 2008/0275457 A1 | 11/2008 | Meek |
| 2009/0112216 A1 | 4/2009 | Leisinger |
| 2009/0112218 A1 | 4/2009 | Mccleary |
| 2009/0187251 A1 | 7/2009 | Justin |
| 2009/0228012 A1 | 9/2009 | Gangji |
| 2009/0307887 A1* | 12/2009 | Jones et al. .................. 29/281.5 |
| 2010/0069909 A1 | 3/2010 | Taylor |
| 2010/0107829 A1 | 5/2010 | Zimmerman |
| 2010/0145345 A1 | 6/2010 | Ammann |
| 2010/0168752 A1 | 7/2010 | Edwards |
| 2010/0249943 A1 | 9/2010 | Bergin |
| 2011/0054628 A1 | 3/2011 | Banks |
| 2011/0071527 A1 | 3/2011 | Nelson |
| 2011/0302760 A1 | 12/2011 | Leisinger |
| 2012/0053698 A1 | 3/2012 | Huff |
| 2012/0259341 A1 | 10/2012 | McCleary |
| 2012/0259421 A1 | 10/2012 | Satterthwaite |

FOREIGN PATENT DOCUMENTS

| | | |
|---|---|---|
| DE | 3538654 A1 | 4/1987 |
| DE | 10014401 A1 | 6/2001 |
| DE | 20114835 U1 | 1/2002 |
| DE | 202006000845 U1 | 5/2006 |
| DE | 202012102017 U1 | 10/2013 |
| EP | 206777 A2 | 12/1986 |
| EP | 239711 A1 | 10/1987 |
| EP | 333990 A2 | 9/1989 |
| EP | 511244 A1 | 11/1992 |
| EP | 595956 A1 | 5/1994 |
| EP | 661023 A2 | 7/1995 |
| EP | 726063 A1 | 8/1996 |
| EP | 728449 A2 | 8/1996 |
| EP | 842639 A2 | 5/1998 |
| EP | 861635 A2 | 9/1998 |
| EP | 1000595 A1 | 5/2000 |
| EP | 1013245 A2 | 6/2000 |
| EP | 1080701 A2 | 3/2001 |
| EP | 1084680 A2 | 3/2001 |
| EP | 1191906 A1 | 4/2002 |
| EP | 1201191 A1 | 5/2002 |
| EP | 1263334 A2 | 12/2002 |
| EP | 1323395 A2 | 7/2003 |
| EP | 1348384 A2 | 10/2003 |
| EP | 1369089 A2 | 12/2003 |
| EP | 1435223 A1 | 7/2004 |
| EP | 1493407 A2 | 1/2005 |
| EP | 1591084 A1 | 11/2005 |
| EP | 1738723 A1 | 1/2007 |
| EP | 1905396 A1 | 4/2008 |
| EP | 1522284 A1 | 12/2008 |
| EP | 2055273 A1 | 5/2009 |
| EP | 2057969 A2 | 5/2009 |
| FR | 2606628 A1 | 5/1988 |
| FR | 2699400 A1 | 6/1994 |
| FR | 2737107 A1 | 1/1997 |
| FR | 2828397 A1 | 2/2003 |
| FR | 2832624 A1 | 5/2003 |
| FR | 2926208 A1 | 7/2009 |
| FR | 2926212 B1 | 3/2010 |
| GB | 250441 A | 6/1992 |

(56) References Cited

FOREIGN PATENT DOCUMENTS

| | | |
|---|---|---|
| JP | 5212069 A | 8/1993 |
| JP | 6500039 A | 1/1994 |
| JP | 10080095 A | 3/1998 |
| JP | 2000210314 A | 8/2000 |
| JP | 2002153479 A | 5/2002 |
| JP | 2002238912 A | 8/2002 |
| JP | 2003339724 A | 12/2003 |
| JP | 2004223261 A | 8/2004 |
| JP | 2004251450 A | 9/2004 |
| JP | 2006501917 T | 1/2006 |
| JP | 2006523106 A | 10/2006 |
| JP | 2007061154 A | 3/2007 |
| JP | 2007503911 A | 3/2007 |
| JP | 2007508063 A | 4/2007 |
| JP | 2010540179 A | 12/2010 |
| JP | 5148516 B2 | 2/2013 |
| WO | WO 9110408 A1 | 7/1991 |
| WO | WO 9210138 A1 | 6/1992 |
| WO | WO 9301769 A1 | 2/1993 |
| WO | WO 9412123 A1 | 6/1994 |
| WO | WO 9427507 A1 | 12/1994 |
| WO | WO 9615738 A1 | 5/1996 |
| WO | WO 9615739 A1 | 5/1996 |
| WO | WO 9920196 A1 | 4/1999 |
| WO | WO 0167997 A1 | 9/2001 |
| WO | WO 02102254 A2 | 12/2002 |
| WO | WO 03015642 A1 | 2/2003 |
| WO | WO 03065906 A2 | 8/2003 |
| WO | WO 03082159 A1 | 10/2003 |
| WO | WO 03092513 A1 | 11/2003 |
| WO | WO 03094698 A2 | 11/2003 |
| WO | WO 03094803 A1 | 11/2003 |
| WO | WO 2004028266 A1 | 4/2004 |
| WO | WO 2004032767 A1 | 4/2004 |
| WO | WO 2004089224 A2 | 10/2004 |
| WO | WO 2005034817 A1 | 4/2005 |
| WO | WO 2007026119 A1 | 3/2007 |
| WO | WO 2007098549 A1 | 9/2007 |
| WO | WO 2007106752 A1 | 9/2007 |
| WO | WO 2008069800 A1 | 6/2008 |
| WO | WO 2009024798 A1 | 2/2009 |
| WO | WO 2012138824 A2 | 10/2012 |

OTHER PUBLICATIONS

S-Rom Modular Hip System, Retrieved From Johnson & Johnson Gateway Web Site http://www.jnj.gateway.com/home.jhtml?loc=ENG&page=viewContent&contented=fc0de0010000030, retrieved on Sep. 26, 2005, 1 page.

Zimmer Fracture Equipment & Orthopaedic Appliances, 1 page, Published At Least As Early As Sep. 29, 2005.

Gray, John R., ;Clinically-Oriented Geometry of the Femur;, A thesis submitted to the School of Physical & Health Education in partial fulfillment of requirements for the degree of Master of Science, Queen's University, Kingston, Ontario, Canada, Aug. 1995, 73 pages.

Paul, H.A., et al. "Development Of A Surgical Robot For Cementless Total Hip Arthroplasty," Clinical Orthopedics & Related Research 285 Dec. 1992: 57-66.

\* cited by examiner

TAPER DISENGAGEMENT TOOL

CROSS REFERENCE TO RELATED CASE

This application is a divisional application of U.S. Utility patent application Ser. No. 11/927,811 entitled "Taper Disengagement Tool", filed on Oct. 30, 2007 by Steven R. Leisinger, (now granted U.S. Pat. No. 8,556,912, issued Oct. 15, 2013), the entirety of which is hereby incorporated by reference.

TECHNICAL FIELD OF THE INVENTION

The present invention relates generally to the field of orthopaedics, and more particularly, to an implant for use in arthroplasty.

BACKGROUND OF THE INVENTION

Patients who suffer from the pain and immobility caused by osteoarthritis and rheumatoid arthritis have an option of joint replacement surgery. Joint replacement surgery is quite common and enables many individuals to function properly when it would not be otherwise possible to do so. Artificial joints are usually comprised of metal, ceramic and/or plastic components that are fixed to existing bone.

Such joint replacement surgery is otherwise known as joint arthroplasty. Joint arthroplasty is a well-known surgical procedure by which a diseased and/or damaged joint is replaced with a prosthetic joint. In a typical total joint arthroplasty, the ends or distal portions of the bones adjacent to the joint are resected or a portion of the distal part of the bone is removed and the artificial joint is secured thereto.

There are known to exist many designs and methods for manufacturing implantable articles, such as bone prostheses. Such bone prostheses include components of artificial joints such as elbows, hips, knees and shoulders.

During performance of a joint replacement procedure, it is generally necessary to provide the surgeon with a certain degree of flexibility in the selection of a prosthesis. In particular, the anatomy of the bone into which the prosthesis is to be implanted may vary somewhat from patient to patient. Such variations may be due to, for example, the patient's age, size and gender. For example, in the case of a femoral prosthesis, the patient's femur may be relatively long or relatively short thereby requiring use of a femoral prosthesis, which includes a stem that is relatively long or short, respectively. Moreover, in certain cases, such as when use of a relatively long stem length is required, the stem must also be bowed in order to conform to the anatomy of the patient's femoral canal.

Such a need for prostheses of varying shapes and sizes thus creates a number of problems in regard to the use of a one-piece prosthesis. For example, a hospital or surgery center must maintain a relatively large inventory of prostheses in order to have the requisite mix of prostheses needed for certain situations, such as trauma situations and revision surgery. Moreover, since the bow of the stem must conform to the bow of the intramedullary canal of the patient's femur rotational positioning of the upper portion of the prosthesis is limited thereby rendering precise location of the upper portion and hence the head of the prosthesis very difficult. In addition, since corresponding bones of the left and right side of a patient's anatomy (e.g. left and right femur) may bow in opposite directions, it is necessary to provide (left) and (right) variations of the prosthesis in order to provide anteversion of the bone stem, thereby further increasing the inventory of prostheses which must be maintained.

As a result of these and other drawbacks, a number of modular prostheses have been designed. As its name implies, a modular prosthesis is constructed in modular form so that the individual elements or figures of the prosthesis can be selected to fit the needs of a given patient's anatomy. For example, modular prostheses have been designed which include a proximal neck component which can be assembled to any one of numerous distal stem components in order to create an assembly which fits the needs of a given patient's anatomy. Such a design allows the distal stem component to be selected and thereafter implanted in the patient's bone in a position which conforms to the patient's anatomy while also allowing for a limited degree of independent positioning of the proximal neck component relative to the patient's pelvis.

One issue that arises as a result of the use of a modular prosthesis is the locking of the components relative to one another. In particular, firm reproducible locking of the proximal neck component to the distal stem component is critical to prevent separation of the two components subsequent to implantation thereof into the patient. The need for the firm locking is particularly necessary if the design does not provide for positive locking with weight bearing. As such, a number of locking mechanisms have heretofore been designed to lock the components of a modular prosthesis to one another. For example, a number of modular prostheses have heretofore been designed to include a distal stem component, which has an upwardly extending post, which is received into a bore defined distal neck component. A relatively long fastener such as a screw or bolt is utilized to secure the post with the bore. Other methods of securing modular components include the impacting of one component onto the other. This method has highly variable results.

Current designs of modular stems include designs in which the modular connection utilizes a tapered fit between the two components. For example, the proximal body may include an internal taper, which mates with an external taper on the distal stem. Such a taper connection may be used in conjunction with additional securing means, for example, a threaded connection or may be used alone. It is important that the tapered connection be secure. For example, the proper amount of force must be applied to the tapered connection to properly secure the tapered connection so that the connection can withstand the forces associated with the operation of the stem.

In certain instances, it may be desired to disassociate the two components. For example, after the surgery, if there are problems with the implant, the surgeon may need to do a revision that would require removing the original proximal body from the stem. Other times, the surgeon may discover after assembling the proximal body and the stem that a different sized stem or body would be more appropriate. In such instances, the surgeon would have to disassemble the stem from the body. In these cases, removing the proximal body from the stem can be very difficult. Because the tapered connection is so secure, it requires a great amount of force to disassociate the components. In some designs, the surgeon may have to apply 2000 pounds of axial force in order to separate the components.

There are currently some disengagement tools in use for disassociating the proximal body from the distal stem. However, these devices have proven to be unsuccessful. Some of the current devices may even break the components.

Therefore, there is a need for a tool that allows a surgeon to easily and safely disengage the taper lock between the proximal body and the distal stem.

SUMMARY OF THE INVENTION

According to one embodiment of the present invention, a disassembly tool for disassembly of a first component of a prosthesis from a second component of the prosthesis for use in joint arthroplasty is provided. The tool includes a body having an internal bore. At least a portion of the internal bore is threaded for engagement with a thread on the first component of the prosthesis. The tool also includes an expandable ring surrounding a portion of the body and adapted to engage the first component, such that when a radial force is applied to the body, the ring expands, applying an axial force against the first component.

According to another embodiment of the present invention, a method of disassembling a first and second component of a prosthesis used in joint arthroplasty is provided. The method includes providing a first component having a male taper and a second component having an internal bore with a female taper. The first component and second component are engaged via the male and female tapers. A disassembly tool is inserted into the inner bore of the second component. The disassembly tool has a body and an expandable portion. The body is coupled to the first component. Through a frictional force the expandable portion and an inner diameter of the second component become engaged. The threaded internal bore of the disassembly tool is partially dethreaded from the first component. The expandable portion and the inner diameter of the second component expand, disengaging the first component from the second component.

According to yet another embodiment of the present invention, a kit is provided. The kit includes a first component having a male taper and a second component having an internal bore with a female taper. The first component and second component are engageable via the male and female tapers. The kit also includes a disassembly tool having a body and an expandable portion separable from the body, such that the expandable portion has an initial outer diameter equal to the inner diameter of the internal bore of the second component.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which.

DETAILED DESCRIPTION OF THE INVENTION

Embodiments of the present invention and the advantages thereof are best understood by referring to the following descriptions and drawings, wherein like numerals are used for like and corresponding parts of the drawings.

Figures 1, 2, 3:
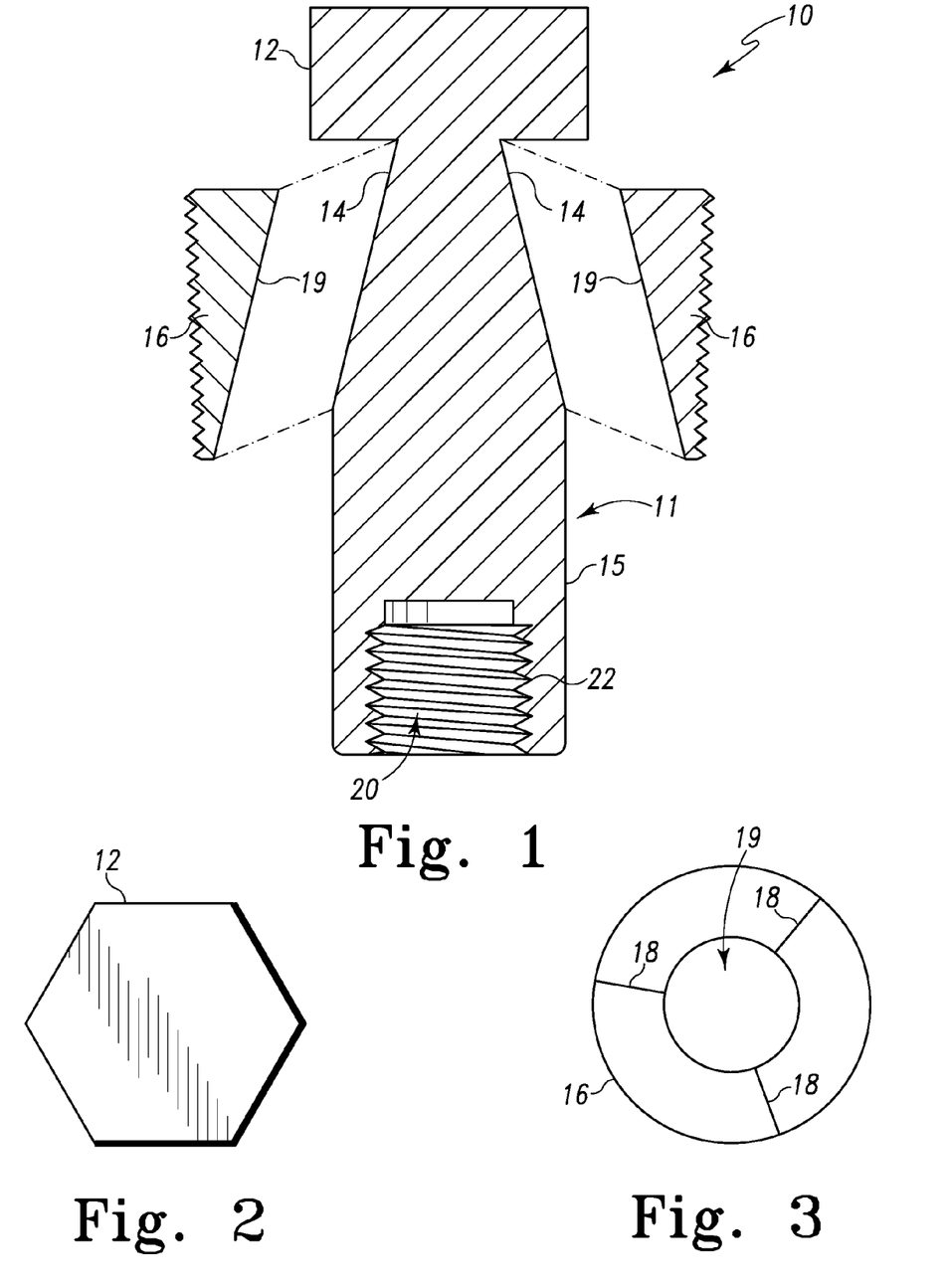
FIG. 1 is a perspective view of a disengagement tool according to one embodiment of the present invention.
FIG. 2 is a top view of the disengagement tool of FIG. 1.
FIG. 3 is a plan view of a two-pieced modular hip stem that may be disassembled with the disassembly tool of FIG. 1.

Referring now to FIG. 1, a disassembly tool 10 according to one embodiment of the present invention is illustrated. The dissambly tool 10 includes a body 11 having a top portion 12, a tapered portion 14, and a bottom portion 15. The tool 10 also includes a ring portion 16 (FIG. 3). As illustrated in the top view of FIG. 2, the top portion 12 is hex-shaped. The hex-shape of the top portion 12 allows the top portion to be grasped by common tools.

Turning back to FIGS. 1 and 3, as shown, the ring 16 is generally cylindrical and includes a plurality of perforations 18. The perforations 18 allow the ring 16 to break into pieces when a force is applied against the ring 16. The ability to break into pieces allows the ring 16 to be inserted into a space that has a greater diameter than the outer diameter of the ring 16. However, if a force is applied that causes the ring 16 to break into pieces, the effective outer diameter of the ring 16 enlarges. As illustrated in FIG. 3, the ring 16 includes an inner bore 19. The bore 19 is tapered in the embodiment illustrated in FIG. 1, but may be non-tapered in other embodiments.

The body 11 also includes an internal bore 20. The internal bore 20 in the embodiment shown in FIG. extends through part of the bottom portion 15. In other embodiments, the bore 20 may extend through the entire body 11. In the embodiment illustrated in FIG. 1, the internal bore 20 includes a threaded portion 22 that extends along the length of the bore 20. In some embodiments, the threaded portion includes clockwise threads—meaning that the threads are designed to engage other threads when rotated in a clockwise fashion and to disengage other threads when rotated in a counter-clockwise fashion.

Figure 4:
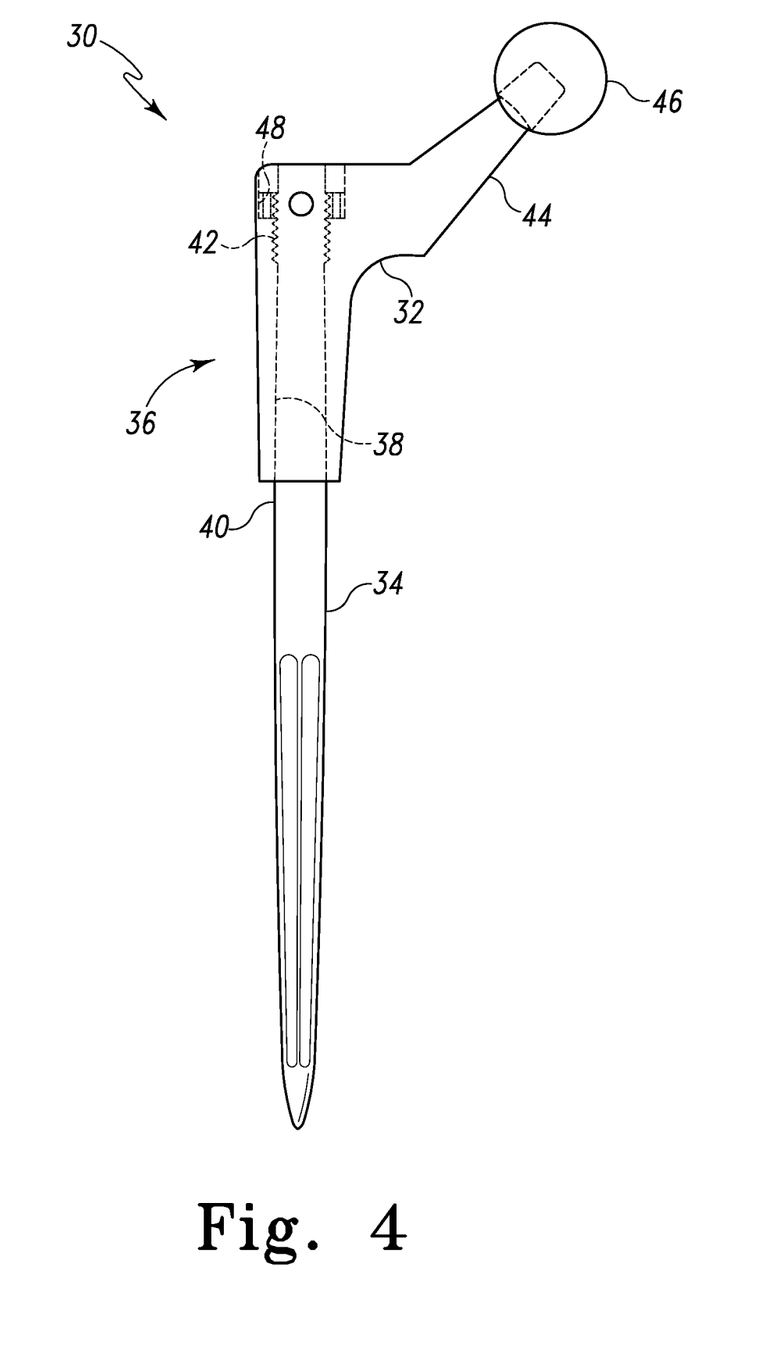
FIG. 4 is a plan view of the modular hip stem of FIG. 3.

Turning now to FIG. 4, a prosthesis 30 is shown in greater detail. The prosthesis 30 as shown in FIG. 4 includes a proximal body 32 and a distal stem 34, which have an interference connection that is, for example, an interference connection of a cylindrical bore to a cylindrical stem, as well as, a splined non-uniform cross-section stem to a splined or non-uniform cross-section opening. It should further be appreciated that the proximal body and distal stem of the prosthesis 30 for use with the assembly tool of the present invention may include a taper connection 36 in which the distal stem 34 has an internal taper 38 and the proximal body 32 has an external taper 40. The taper connection 36 consists of an external taper 40 formed on the distal stem 34 that engages with internal taper 38 formed on the proximal body 32.

The prosthesis 30 as shown may include external threads 42 formed on the distal stem 34. The proximal body 32 may include a neck 44 to which a head 46 may matingly be fitted. As an additional precaution in assuring that the proximal body 32 remains secured to the distal stem 34, the prosthesis 30 may further include a nut 48 which threadably engages the external threads 42 of the distal stem 34.

Figure 5:
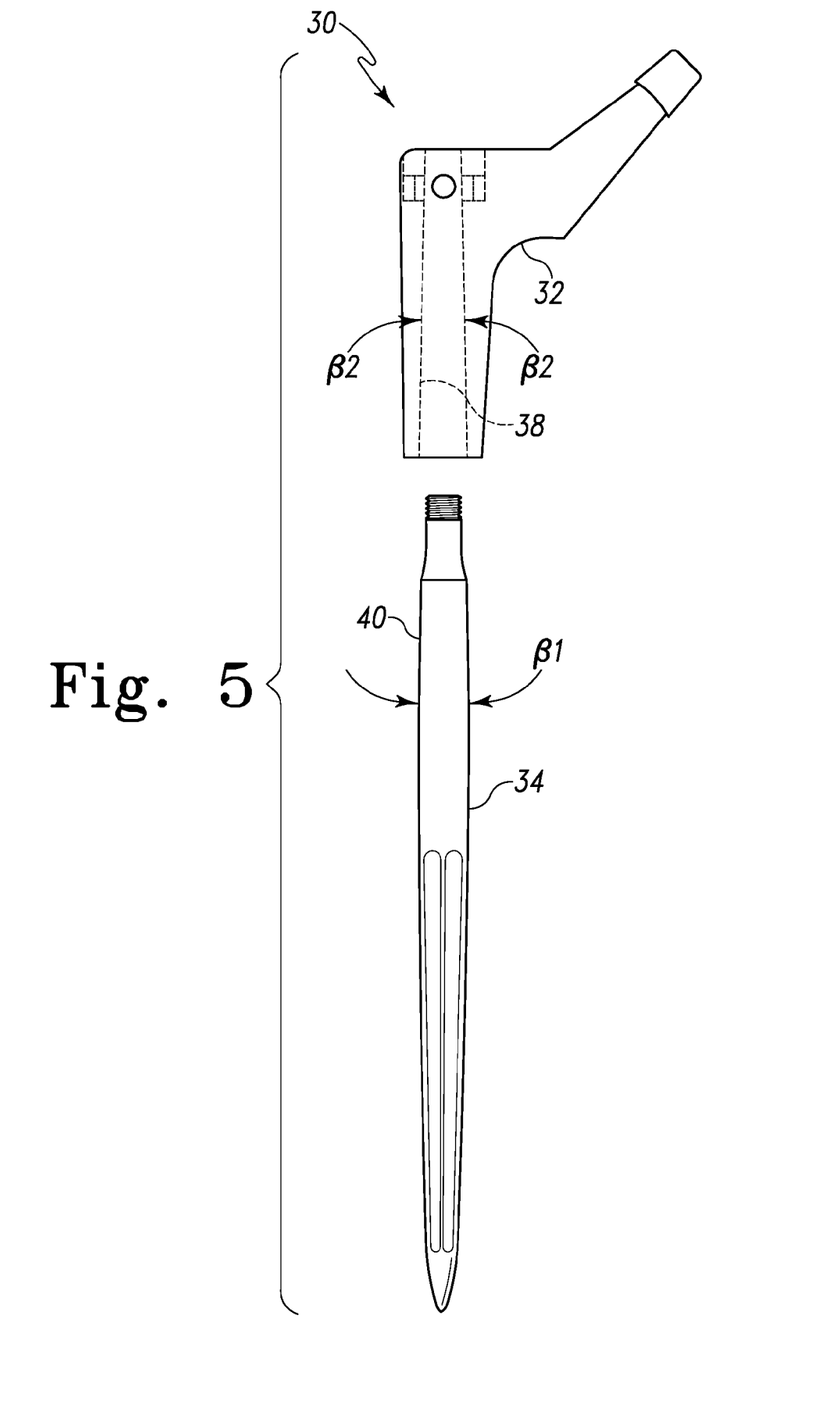
FIG. 5 is an expanded view of the modular hip system of FIG. 3.

Referring now to FIG. 5, the prosthesis 30 is shown with the proximal body 32 disassembled from the distal stem 34. The external taper 40 of the distal stem 34 is defined by an included angle β1. In order that the proximal body 32 fits securely to the distal stem 34, the proximal body 32 includes the internal taper 38 defined by included angle β2. The angles β1 and β2 may be generally the same. Alternatively the taper angle may be divergent. The angles β1 and β2 should be chosen, such that the fit of the proximal body 32 to the distal stem 34 is secure.

As discussed previously in the background section, in some instances, the internal and external tapers 38, 40 lock the proximal body 32 to the distal stem 34. This can be problematic should the surgeon need to disengage the proximal body 32 from the distal stem 34.

Figure 6:
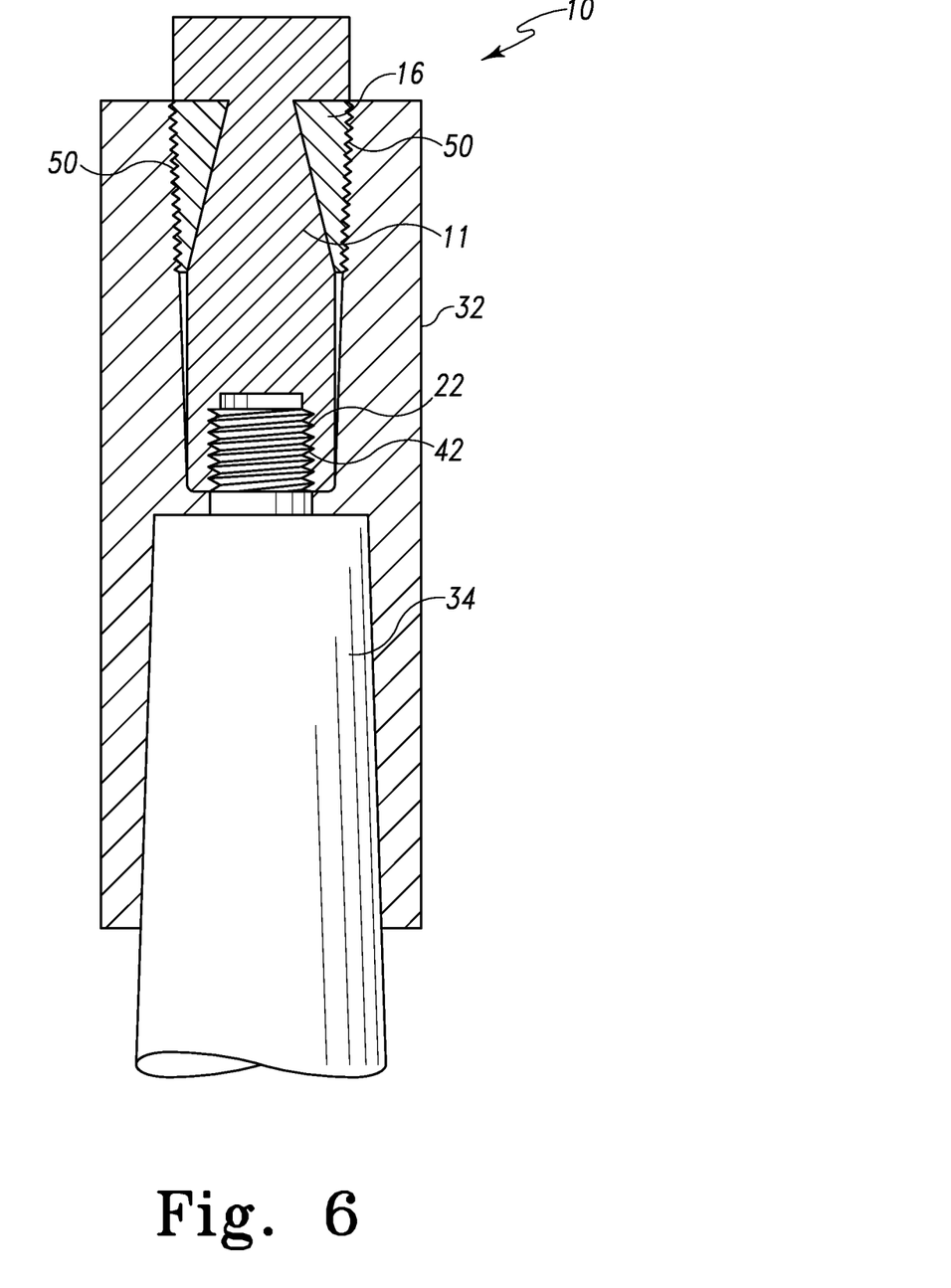
FIG. 6 is a cross-sectional view of a disengagement tool according to one embodiment of the present invention.

Turning now to FIG. 6, the tool 10 is shown inserted into the proximal body 32 and distal stem 34. As shown, the threads 22 of the tool 10 engage the threads 42 of the distal stem 34. The ring 16 is shown in place between the proximal body 32 and the body 11 of the tool 10. The ring 16 may include serrated edges 50 to allow the ring 16 to grasp the inner diameter of the proximal body 32.

Figure 7:
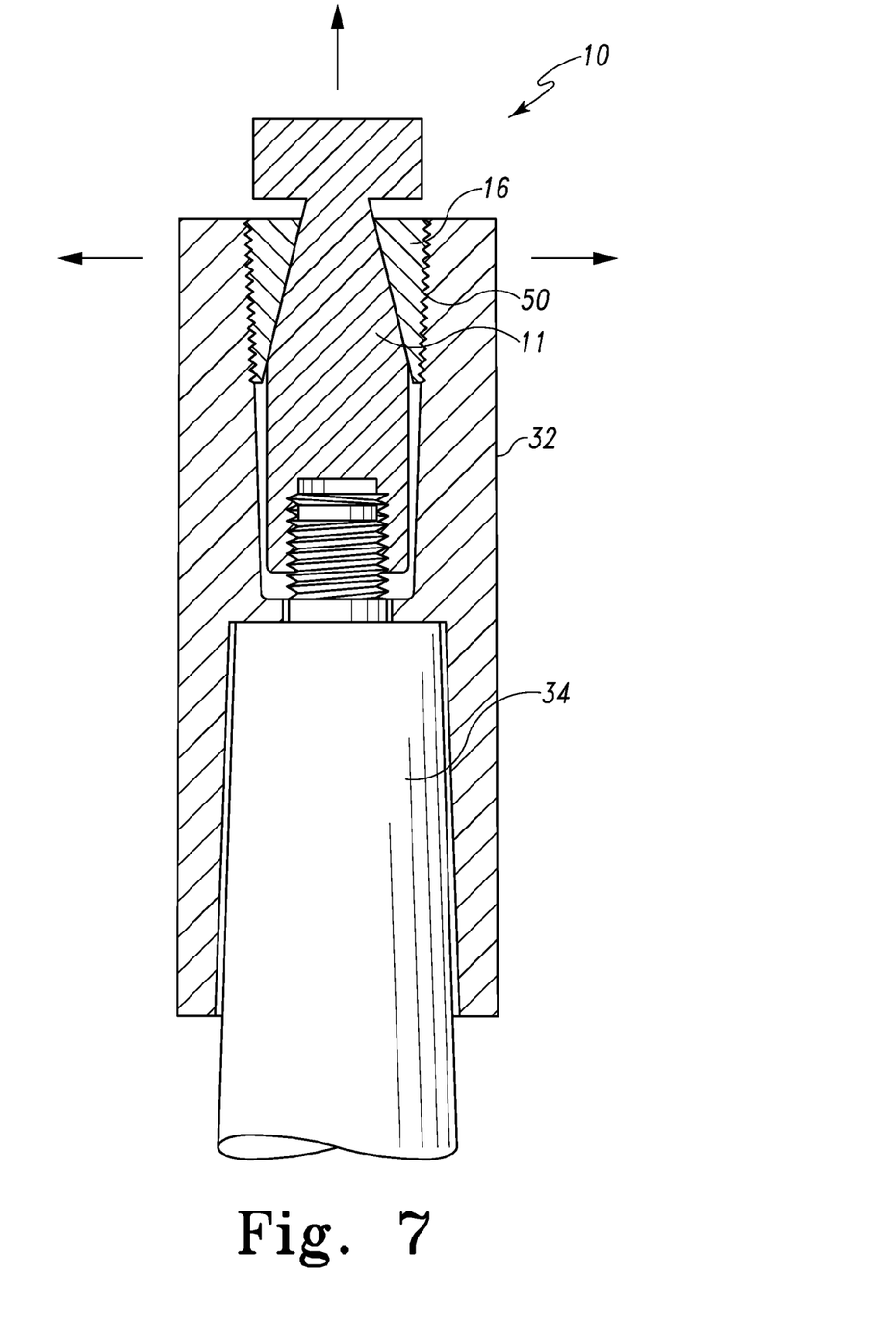
FIG. 7 is a cross-sectional view of a disengagement tool inserted into an implant according to one embodiment of the present invention.

As shown in FIG. 7, when the user turns the body 11 counterclockwise, the threads 22 disengage from the threads 42 of the distal stem and the body 11 moves upward relative to the proximal body 32 and distal stem 34. Because of the serrated edges 50 of the ring 16 grasp the inner diameter of the proximal body 32, the ring 16 does not advance with the body 11. Instead, as the body 11 exerts a radial force against the ring 16, the perofrations 18 (FIG. 3) break, creating three ring pieces that push against the inner diameter of the proximal body 32. As the body 11 turns, the radial force applied to the body translates into an axial force against the inner diameter of the proximal body 32, thereby breaking the taper lock, and allowing the proximal body 32 to be removed from the stem 34.

Therefore, breaking the lock does not require pulling the taper off-center or using a great amount of force. Merely by utilizing a common wrench, the taper lock can be broken.

In other embodiments, the ring 16 may be broken apart by the insertion of a sleeve (not shown). The sleeve would have a diameter greater than the ring 16 and would force the ring 16 to break into pieces. In yet other embodiments, the ring 16 could include a groove with an elastomer band. As the body 11 is pulled away from the proximal body 32, the elastomer band would keep the ring 16 in place. The user could then use a hollow tube or an impact to disengage the ring 16 from the body 11. Alternatively, some sort of adhesive could be used to keep the ring 16 in place during insertion into the proximal body 32.

In the illustrated embodiment, the bore 19 is tapered at an angle that matches the tapered portion 14 of the body 11. However, in other embodiments, the bore 19 may not be tapered or may be tapered at a different angle.

In the illustrated embodiment the outside of the ring 16 is angled the same as the inside of the proximal body 32. However, in other embodiments, the outside of the ring 16 may have an angle that is different than that of the proximal body 32.

Although the present invention and its advantages have been described in detail, it should be understood that various changes, substitutions, and alterations can be made therein without departing from the spirit and scope of the present invention as defined by the appended claims.

I claim:

1. A method of disassembling a first and second component of a prosthesis used in joint arthroplasty, the method comprising:
    using the first component of the prosthesis having a male taper;
    using the second component of the prosthesis having an internal bore with a female taper, the first component and second component being engaged via the male and female tapers;
    inserting a disassembly tool into an inner bore of the second component, the disassembly tool having a body having an internal bore at one end and being tapered inwardly towards its opposite end, the disassembly tool further having an expandable portion, the expandable portion being an expandable ring having a tapered internal bore;
    coupling the body to the first component;
    engaging, through a frictional force the expandable portion and an inner diameter of the second component;
    partially dethreading a threaded internal bore of the disassembly tool from the first component; and
    expanding the expandable portion and the inner diameter of the second component by moving the tapered portion of the body within the tapered internal bore of the expandable portion, applying a radial force to the body, causing the body to expand to engage the second component, allowing an axial force to be applied through the body against the first component relative to the second component, disengaging the first component from the second component,
    wherein the coupling the body to the first component comprises threading an internal bore of the body onto a threaded post of the first component.

2. The method of claim 1, wherein partially dethreading the threaded internal bore of the disassembly tool comprises disengaging the expandable portion from the body.

3. The method of claim 1, wherein expanding the expandable portion comprises exerting a force against an inner wall of the expandable portion.

4. The method of claim 3, wherein the expanding the expandable portion comprises causing the expandable portion to split into at least two pieces.

5. The method of claim 1, wherein inserting the disassembly tool into the inner bore of the second component comprises inserting the expandable portion separately from inserting the body.

6. A kit comprising:
    a first component having a male taper;
    a second component having an internal bore with a female taper, the first component and second component being engageable via the male and female tapers; and
    a disassembly tool having a body having an internal bore at one end and being tapered inwardly towards its opposite end, the disassembly tool further having an expandable portion separable from the body, such that the expandable portion has an initial outer diameter equal to the inner diameter of the internal bore of the second component, wherein the expandable portion being an expandable ring having a tapered internal bore, so that, when the tapered portion of the body is moved within the tapered internal bore of the ring, a radial force is applied to the ring which causes it to expand radially to engage the second component, allowing an axial force to be applied through the body against the first component relative to the second component, wherein the first component includes a threaded post.

7. The kit of claim 6, wherein internal bore of the body is a threaded bore, adapted to engage the threaded post of the first component.

8. The kit of claim 6, wherein the expandable portion includes serrated edges along its outer diameter, adapted to grip the inner diameter of the internal bore of the second component.

9. The kit of claim 6, wherein the body includes a hex-shaped top portion adapted for engaging tools.

* * * * *